US005546996A

United States Patent [19]

Broyles et al.

[11] Patent Number: 5,546,996
[45] Date of Patent: Aug. 20, 1996

[54] DISPENSING CARTRIDGE REFILLNG SYSTEM

[75] Inventors: Bruce R. Broyles, Oakdale; Cary A. Kipke, Woodbury, both of Minn.; William R. George, Chicago, Ill.

[73] Assignee: Minnesota Mining and Manufacturing Company, St. Paul, Minn.

[21] Appl. No.: 287,841

[22] Filed: Aug. 9, 1994

[51] Int. Cl.⁶ .................................. B65B 1/04; B65B 3/04
[52] U.S. Cl. ........................... 141/18; 141/27; 141/100; 141/114; 141/237; 141/279; 141/350; 141/382; 141/375; 141/387
[58] Field of Search .................. 141/18, 21, 23, 141/26, 27, 100, 114, 237, 242, 263, 279, 312, 349, 350, 367, 382, 383, 384, 386, 369, 375, 387, 388; 222/94, 95, 333, 390

[56] References Cited

U.S. PATENT DOCUMENTS

| | | | |
|---|---|---|---|
| 3,592,360 | 7/1971 | Aleck | 222/95 |
| 3,633,636 | 11/1972 | Schultz | 141/369 |
| 4,199,081 | 4/1980 | Mason | 222/43 |
| 4,255,096 | 3/1981 | Coker, Jr. et al. | 417/415 |
| 4,260,077 | 4/1981 | Schroeder | 222/137 |
| 4,274,453 | 6/1981 | Lee | 141/392 |
| 4,421,146 | 12/1983 | Bond et al. | 141/349 |
| 4,434,820 | 3/1984 | Glass | 141/2 |
| 4,750,532 | 6/1988 | Grothoff | 141/27 |
| 4,974,756 | 12/1990 | Pearson et al. | 222/562 |
| 5,082,444 | 1/1992 | Rhoades et al. | 433/80 |
| 5,092,492 | 3/1992 | Centea | 222/137 |
| 5,098,291 | 3/1992 | Curtis et al. | 433/89 |
| 5,203,476 | 4/1993 | Keller | 222/136 |
| 5,246,367 | 9/1993 | Ito et al. | 433/80 |
| 5,269,762 | 12/1993 | Armbruster et al. | 604/155 |
| 5,289,949 | 3/1994 | Gentile | 222/137 |
| 5,297,962 | 3/1994 | O'Connor et al. | 433/89 |
| 5,304,165 | 4/1994 | Haber et al. | 604/411 |

FOREIGN PATENT DOCUMENTS

| | | |
|---|---|---|
| 0465267 | 1/1992 | European Pat. Off. . |
| 0563486 | 10/1993 | European Pat. Off. . |
| 0586342 | 3/1994 | European Pat. Off. . |
| 0591098 | 4/1994 | European Pat. Off. . |
| 0607102 | 7/1994 | European Pat. Off. . |
| 996467 | 6/1965 | United Kingdom . |
| 1233688 | 5/1971 | United Kingdom . |

OTHER PUBLICATIONS

ESPE Pentamix brochure, ESPE Premier Sales Co., (undated).
European Search Report for EP 95 11 2028 (USSN 08/287, 841).

Primary Examiner—Henry J. Recla
Assistant Examiner—Steven O. Douglas
Attorney, Agent, or Firm—Gary L. Griswold; Walter N. Kirn; James D. Christoff

[57] ABSTRACT

A dispenser refilling system includes a bulk container for refilling a cartridge of a dispenser, so that the cartridge need not be disposed of after a single use. The system preferably includes one or more fill tubes that are movable by lever operation for extension into the chamber of the cartridge when desired. Each fill tube couples to a piston in the cartridge and directs the component to be replenished in the cartridge chamber through a port in the piston. In certain embodiments, the system includes two bulk containers and a dual chamber dispensing cartridge, and structure is provided to prevent inadvertently reversing the position of the cartridge and for insuring placement of the containers in proper receptacles.

33 Claims, 8 Drawing Sheets

DISPENSING CARTRIDGE REFILLNG SYSTEM

BACKGROUND OF THE INVENTION

1. Field of the Invention

This invention relates to a system for refilling a dispensing cartridge with material made of one or more components.

2. Description of the Related Art

Dispensers are used in a variety of fields for applying a liquid or semi-liquid material directly to a work site or other area as desired. Dispensers that are adapted for hand-held use are especially advantageous because the dispenser can be maneuvered as needed to apply the dispensed material at a particular location. However, the amount of material contained in hand-held dispensers is somewhat limited, because the material together with the container should not weigh more than the hand can comfortably carry.

Some dispensers include replaceable cartridges that contain the material to be dispensed. Examples include caulking guns and other applicators for home, construction or industrial use, and certain syringes and dispensers used in medical and dental fields. The use of cartridges is often considered convenient because contact with the material in the cartridges can be avoided. Unfortunately, such cartridges are often not recycled and consequently contribute to problems associated with solid waste. Purchasing material in cartridges is also somewhat costly due to the cost of the cartridge and the relatively small amount of material contained in the cartridge.

Dispensers having cartridges with dual chambers are typically used to dispense material made of two or more components. In many instances, the dispenser includes an exit conduit that is coupled to outlets of the chambers. The exit conduit contains a static mixer (or optionally a dynamic mixer) for mixing the components during passage through the exit conduit, so that hand mixing can be avoided.

Examples of dual chamber cartridge dispensers are described in U.S. Pat. Nos. 4,995,540 and 5,005,735. In general, such dispensers include a pair of side-by-side plungers that are advanced by a ratchet mechanism to simultaneously push respective pistons in the chambers of the cartridge and direct the components in both chambers toward the exit conduit containing the mixer. Linkage of the pistons together helps insure that the components are discharged and mixed in the proper ratio (such as 1:1) as might be specified by the manufacturer.

Dual chamber cartridge dispensers are widely used in the field of dentistry to deliver impression material to an impression tray or, on occasion, directly into the oral cavity. Recently, there has also been increased interest in using dual chamber cartridge dispensers in the field of audiology for dispensing material used in taking an impression of the outer ear canal in order to make a custom-fitted hearing aid. Dispensers having dual chamber cartridges are also used in construction fields, automotive trades and industrial applications for dispensing materials such as epoxies, sealers and coatings made of two or more components that are mixed immediately before use or application.

The use of dual chamber cartridge dispensers for mixing and dispensing material made of two components helps avoid problems often associated with estimation and hand mixing of components provided in separate tubs, tubes or other types of containers. Additionally, human contact with the components or the mixed material need not occur when using such dispensers, an advantage from the standpoint of infection control in the medical or dental fields because the potential for contamination of the components or material is reduced. Reduction of human contact with the components or the mixed material also reduces the likelihood of an allergic or toxic reaction.

However, dual chamber cartridges, like single chamber cartridges, are normally disposed of after a single use and as such create problems associated with solid waste. Furthermore, there is often a small amount of material that remains in the used cartridge that cannot be ejected by the dispenser.

Another disadvantage associated with cartridge dispensing systems occurs during instances when the cartridge is not completely full at the beginning of the dispensing operation, and the need arises to replace the cartridge mid-way through the dispensing operation. Interruption of the dispensing operation to replace the cartridge is often inconvenient and may unduly reduce the opportunity to work with the material as might be desired before setting or curing occurs.

SUMMARY OF THE INVENTION

The present invention concerns a system for refilling dispensing cartridges, including single chamber and dual chamber cartridges. The system includes one or more bulk containers that are used to economically refill the cartridge so that a single cartridge may be used a number of times. As a result, the refilling station reduces the amount of solid waste that might otherwise be associated with single-use cartridges. Moreover, reuse of the cartridge avoids discarding the small amount of components that normally remain in the cartridge after attempts have been made to empty the cartridge. The refilling system is relatively compact and especially adapted for use on a bench top, work station or other area.

One aspect of the present invention concerns a dual chamber dispensing cartridge refilling system that comprises a housing having a first receptacle, a second receptacle and a third receptacle. A first container is releasably received in the first receptacle and contains a quantity of a first component. A second container is releasably received in the second receptacle and contains a quantity of a second component. A dual chamber dispensing cartridge is releasably received in the third receptacle, and includes a first elongated chamber for receiving the first component and a second elongated chamber for receiving the second component. A first tubing is in communication with the first container when the first container is received in the first receptacle. The first tubing is also in communication with the first chamber of the cartridge when the cartridge is received in the third receptacle. A second tubing is in communication with the second container when the second container is received in the second receptacle. The second tubing is also in communication with the second chamber of the cartridge when the cartridge is received in the third receptacle. Means are provided for directing the first component from the first container, through the first tubing and into the first chamber, and for directing the second component from the second container, through the second tubing and into the second chamber. Structure is also provided for substantially precluding the second container from being received in the first receptacle in order to avoid directing the second component into the first chamber of the cartridge.

Another aspect of the present invention concerns a dual chamber dispensing cartridge refilling system that comprises a housing having a first receptacle, a second receptacle and a third receptacle. A first container is releasably received in the first receptacle and contains a quantity of a first component. A second container is releasably received in the second receptacle and contains a quantity of a second component. A dual chamber dispensing cartridge is releasably received in the third receptacle, and includes a first elongated chamber for receiving a first component and a second elongated chamber for receiving a second component. A first elongated fill tube is provided and is in communication with the first container when the first container is received in the first receptacle. A second elongated fill tube is provided and is in communication with the second container when the second container is received in the second receptacle. Means are provided for selectively moving the first fill tube and the second fill tube relative to the cartridge and to respective orientations wherein the first fill tube extends into the first chamber and the second fill tube extends into the second chamber. Means is also provided for directing the first component from the first container, through the first fill tube and into the first chamber, and for directing the second component from the second container, through the second fill tube and into the second chamber. Structure is also provided for substantially precluding the first fill tube from extending into the second chamber.

The present invention also concerns a dispensing cartridge refilling system that comprises a housing having a receptacle, and a dispensing cartridge releasably received in the receptacle. The cartridge includes an elongated chamber for receiving material to be dispensed, and the cartridge includes a piston received in the chamber. A source of material is provided to be dispensed, and a fill tube is in communication with the source of material. At least one of the fill tube and the cartridge is selectively movable relative to the other and to an orientation wherein the fill tube extends into the chamber. The piston includes a port in contact with the fill tube when the fill tube extends into the chamber for enabling material to be directed through the fill tube, through the port and into the chamber.

The present invention also concerns a dispensing cartridge refilling system that comprises a housing having a receptacle, and a container releasably received in the receptacle. The container contains a quantity of material to be dispensed and includes a neck. Tubing is connected to the housing, and the tubing includes a first end located next to the receptacle and a second end for communication with a cartridge to be refilled. A coupler is provided for releasably coupling the neck of the container to the first end of the tubing. The coupler includes a movable element and a spring for urging the element toward a position in contact with the neck when the container is received in the receptacle.

The invention is also directed to a dual chamber dispenser and dispenser refilling system assembly that includes a dispenser having a cartridge with a first chamber, a second chamber, a first plunger received in the first chamber and a second plunger received in the second chamber. The assembly also includes a dispenser refilling system that comprises a source of a first component and a source of a second component. A connector is provided for releasably connecting the dispenser to the refilling system. Means are provided for directing the first component from the source of first component and into the first chamber, and for directing the second component from the source of second component and into the second chamber. Structure is also provided for substantially precluding the second component from being received in the first chamber.

Other aspects and advantages of the invention will be realized after a review of the drawings and the following detailed description.

DETAILED DESCRIPTION OF THE PREFERRED EMBODIMENTS

A dispensing cartridge refilling system 20 is illustrated in FIGS. 1–9 and includes a housing 22 made of a material such as plastic. The housing 22 is relatively compact and adapted for placement on a bench top, work station or other type of table.

Figure 1:
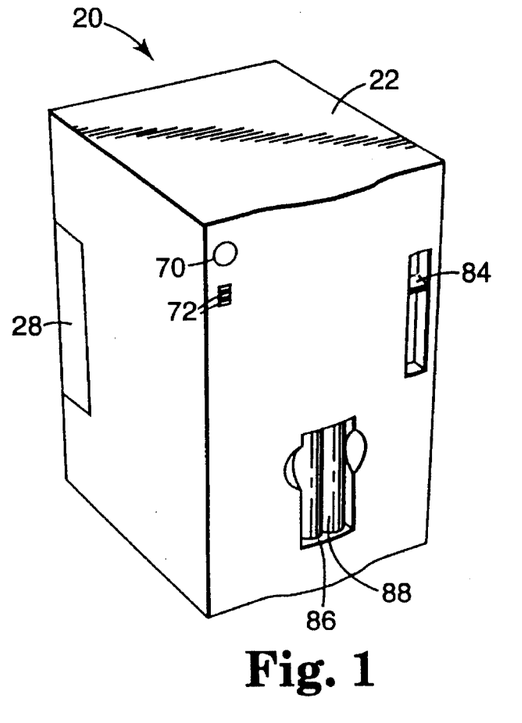
FIG. 1 is a top, front and left side perspective view of a cartridge refilling system according to the present invention.
Figure 2:
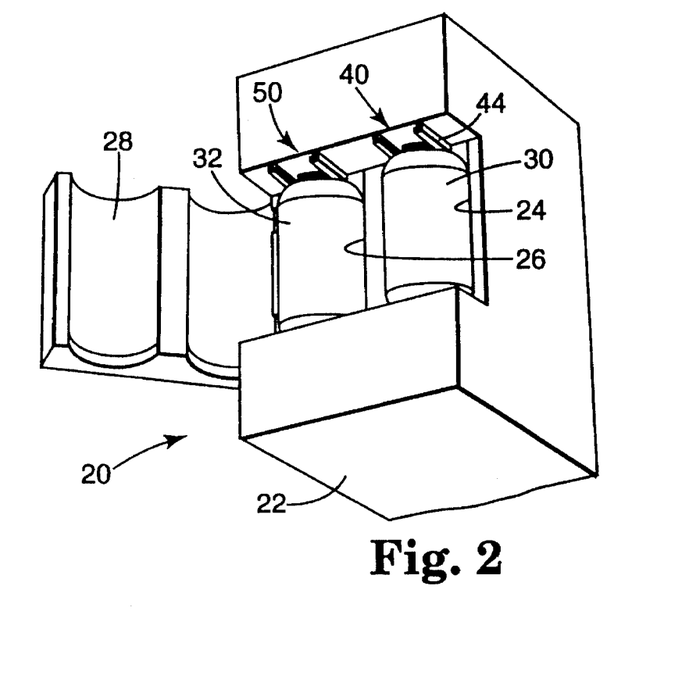
FIG. 2 is a bottom, rear and left side perspective view of the system shown in FIG. 1.

The housing 20 includes a first receptacle 24 and a second receptacle 26 as shown, for example, in FIG. 2. A cover 28 is pivotally connected to the housing 22 for swinging movement about a vertical axis from a closed position that is shown in FIG. 1 and to an open position that is shown in FIG. 2.

A first container 30 is releasably received in the first receptacle 24 and contains a quantity of a first component of the material to be dispensed. A second container 32 is received in the second receptacle 26 and contains a quantity of a second component of the material to be dispensed.

The containers 30, 32 are of the type known as "chub" or "sausage" packs, and are made of flexible sheet-like material such as aluminum foil or metallized plastic so that sidewalls of the containers 30, 32 can be collapsed to eject the components. Each container 30, 32 contains when full about 300–600 ml and preferably about 500 ml of a component, although other sizes are, of course, possible.

Figure 3:
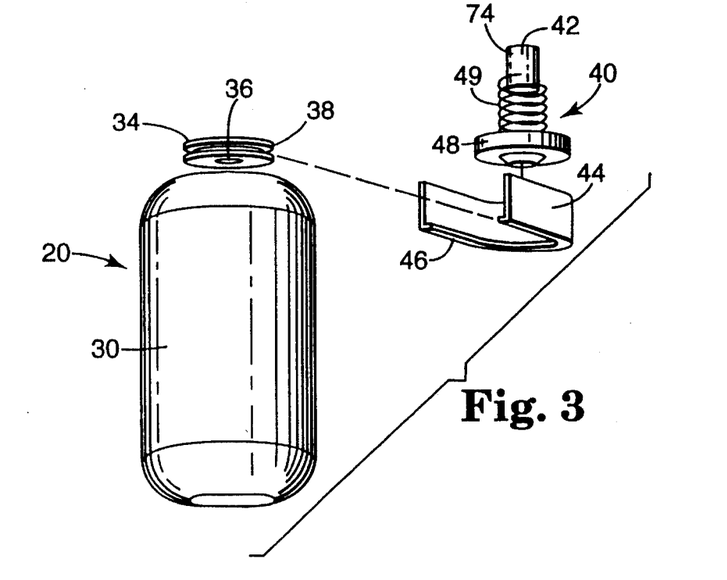
FIG. 3 is an enlarged, exploded perspective view illustrating one of a pair of bulk containers shown in FIG. 2 along with a coupler for releasably coupling the container to a length of tubing of the system.

An exploded view of the first container 30 is illustrated in FIG. 3. The container 30 includes a relatively rigid neck 34 that is affixed (by, for example, an adhesive) to the relatively flexible sheet-like material of the container 30. The neck 34 is generally round and includes a central outlet 36 as well as a circumscribing groove 38.

Figure 8:
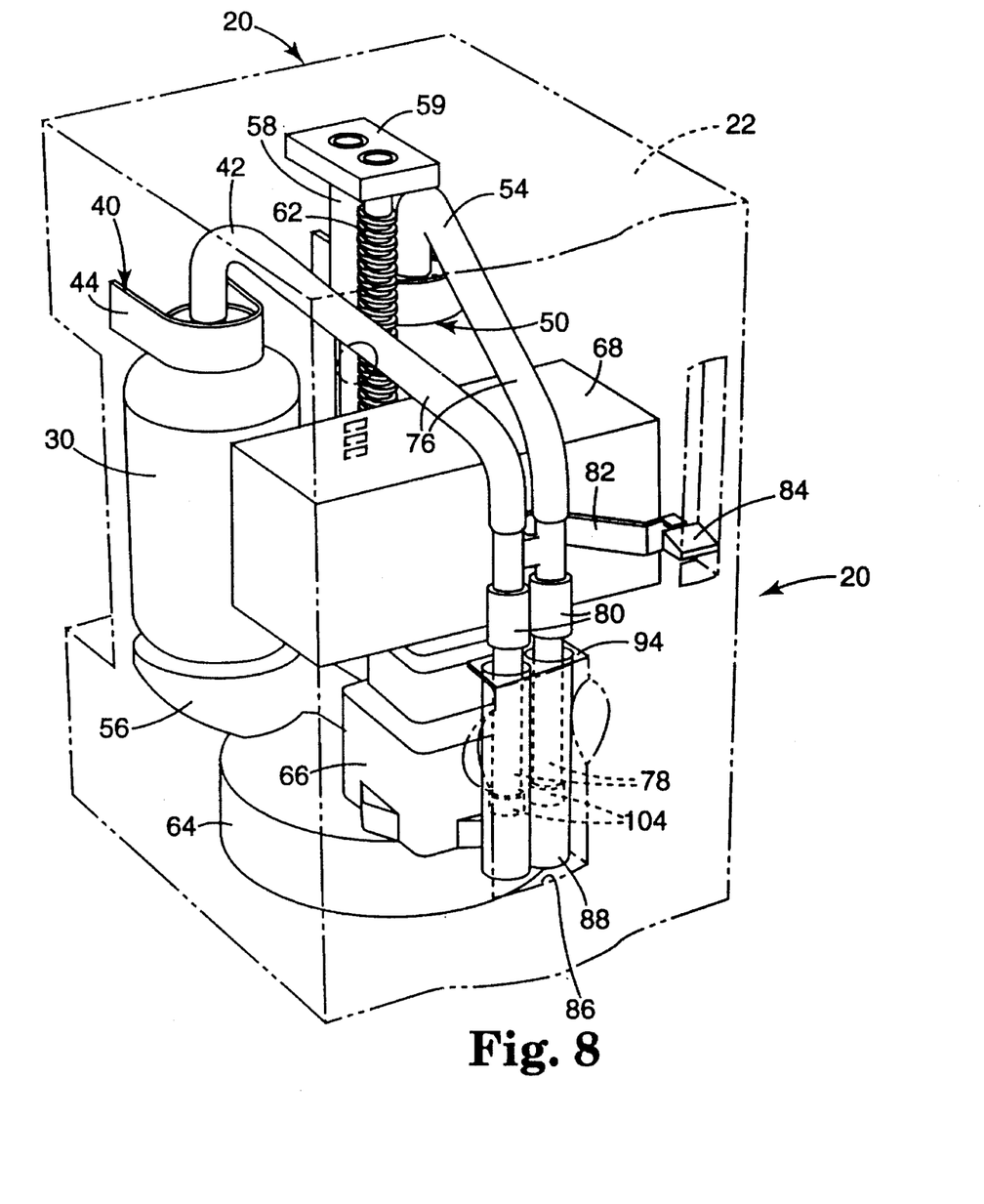
FIG. 8 is an enlarged perspective view somewhat similar to FIG. 1 except that elements within an outer housing of the system are shown and the housing is illustrated by dashed lines, and the fill tubes have been lowered to the position depicted in FIG. 7.

The system 20 includes a coupler 40 for releasably coupling the neck 34 of the first container 30 to a first end of a first length of tubing 42 (see also FIG. 8). The coupler 40 includes a generally U-shaped support 44 having an inwardly extending flange 46 (FIG. 3) for mating reception with the groove 38 of the neck 34. The support 44 is secured to the housing 22 as illustrated in FIG. 2.

The coupler 40 also includes a generally round, movable element 48 having a protruding, chamfered opening for mating contact with the outlet 36 of the container 30. The element 48 is secured to the first end of the first length of tubing 42 in such a fashion that the inlet of the element 48 communicates with the channel within the tubing 42. A coil spring 49 biases the element 48 in a downwardly direction in contact with the neck 34 when the container 30 is received in the support 44.

A second coupler 50 is provided for releasably coupling a neck 52 of the second container 32 to a first end of a second length of tubing 54. The neck 52 and the coupler 50 are somewhat similar in shape to the neck 34 and the coupler 40 respectively, but are constructed with slightly different dimensions so that the neck 52 of the second container 32 does not matingly fit with the first coupler 40, and the neck 34 of the first container 30 does not matingly fit with the second coupler 50.

To this end, the neck 52 is smaller in overall diameter than the neck 34, and the inwardly directed flange of the support of the second coupler 50 is also smaller but sized to matingly fit with the neck 52. The dimensions of the neck 52 and the support flange of the coupler 50 are selected such that neck 34 is too large to fit in the support of the second coupler 50. Likewise, the diameter of the neck 52 is sufficiently smaller than the inner diameter of the flange 46 of the first coupler 40, so that the support 44 is unable to stably latch and connect with the neck 52. The differing dimensions of the necks 34, 52 and the couplers 40, 50 prevent the second component from entering the first length of tubing 42 and the first component from entering the second length of tubing 54.

Figure 4:
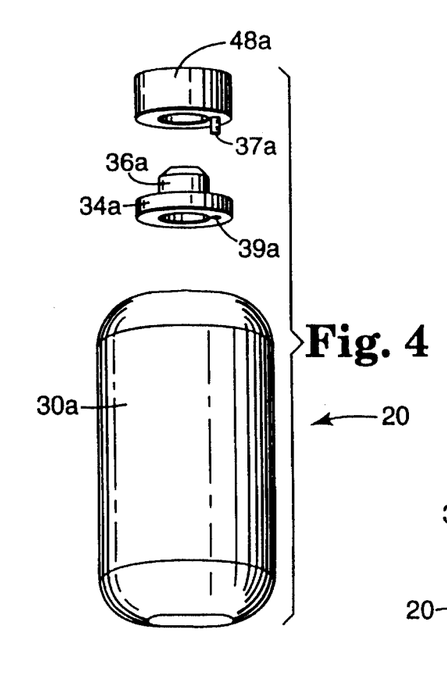
FIG. 4 is a view somewhat similar to FIG. 3 except in accordance with another embodiment of the invention.

An alternate coupling arrangement is illustrated in FIG. 4, wherein a relatively rigid neck 34a of a collapsible first container 30a has a protruding, upwardly extending outlet 36a with a beveled upper end. A keyway 37a comprises a rigid metal pin that depends from a cylindrical element 48a connected to the housing 22 in fixed relation. The keyway 37a is received in a matching hole 39a of a lower, annular portion of the neck 34a. The element 48a also includes a cylindrical bore to matingly receive the protruding outlet 36a.

Although not shown, an inverse construction opposite that depicted in FIG. 4 may be utilized for the second container. More particularly, the neck of such a container may have a cylindrical bore and an adjacent upstanding keyway or pin, and the element that is secured to the housing 22 may have a protruding inlet and an adjacent hole. In this manner, the second container can not be connected to the first outlet and vice versa.

As another option, a construction similar to that shown in FIG. 4 may be utilized with both containers and couplers, except that the neck of each container may have two or more keyways. However, the keyways are oriented in different rotative positions about a vertical axis. For example, the neck of one container may have two keyways that are 90 degrees apart, while the neck of the other container may have two keyways that are 120 degrees apart. The keyways prevent inadvertent coupling of the first container to the second coupler and vice versa.

Figure 5:
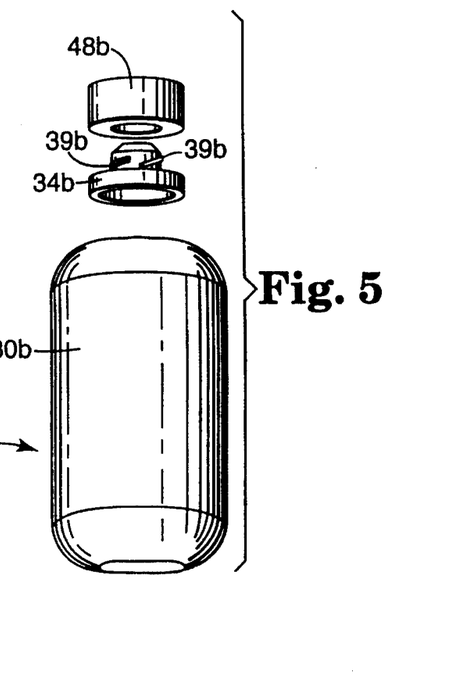
FIG. 5 is a view somewhat similar to FIG. 3, showing another embodiment of the invention.
Figure 6:
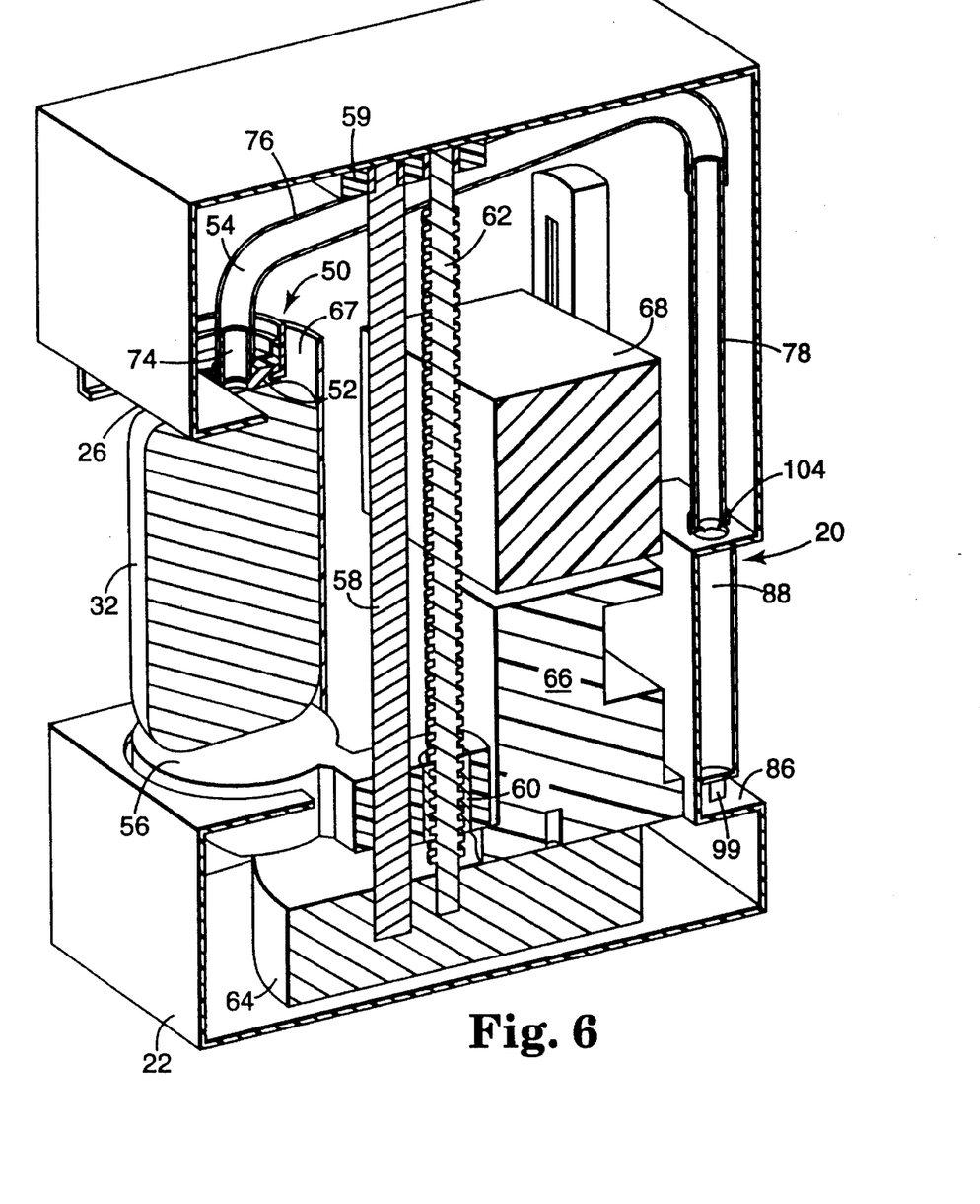
FIG. 6 is an enlarged perspective sectional view of the system shown in FIGS. 1 and 2 except that a rear cover has been removed.

Another embodiment of the invention is illustrated in FIG. 5, wherein a neck 34b of a collapsible first container 30b includes an upwardly extending outlet with a pair of spaced apart threads 39b. The outlet and the threads 39b mate with a cylindrical bore and respective channels formed in an element 48b that is secured to the housing 22. Upon rotation of the container relative to the element 48b, the container is releasably secured in place in the receptacle.

The second container may also have a neck somewhat similar to that shown in FIG. 5, except with threads of a different configuration or in different spatial relationship to each other. Likewise, the element for receiving the second container has an internal configuration adapted to mate with the neck including the threads of such a container. Again, as can be appreciated, such construction helps insure that the first container is not connected to the element of the second receptacle and vice versa.

Referring now to FIGS. 6–9, both of the containers 30, 32 are supported on their lower end in the receptacles 24, 26 respectively by corresponding cylindrical extensions of a single platen 56. A central portion of the platen 56 has a cylindrical bore that receives a stationary, vertical guide shaft 58 that is fixed on its upper end to a support member 59 secured to the housing 22. The central portion of the platen 56 also carries a captured drive nut 60 having a threaded portion that mates with a vertical, threaded drive screw 62.

The upper end of the drive screw 62 is received in a second hole of the support member 59, and is rotatable with respect to the support member 59. A lower end of the drive screw 62 is connected to an output drive of a gear mechanism 64. A housing of the gear mechanism 64 is provided with a bore to provide fixed support for the lower end of the stationary guide shaft 58.

A reversible electric AC motor 66 has an output drive shaft that is coupled to an input drive of the gear mechanism 64. When the motor 66 is energized, the drive screw 62 rotates about its vertical axis and causes the platen 56 to ascend along the guide shaft 58. As the platen 56 rises, the sidewalls of the containers 30, 32 are collapsed in accordion-like fashion and the first and second components are ejected through the container necks 34, 52 and into the tubing 42, 54 respectively.

Preferably, the receptacles 24, 26 have generally cylindrical side walls with a shape that matches the initial shape of the containers 30, 32. To this end, the inner side of the cover 28 is provided with two cylindrical half-sections as shown in FIG. 2. The housing 22 also is provided with two cylindrical half-sections 67 (one of which is partially shown in FIG. 6) that abut the sides opposite the sides of the containers 30, 32 that are shown in FIG. 2. The cylindrical half-sections of the cover 28 and the half-sections 67 facilitate uniform, predictable collapse of the containers 30, 32 without undue bulging in lateral (i.e., horizontal) directions. Hidden receptacles such as covered receptacles 24, 26 are preferred, although receptacles where the containers are partially or fully exposed may also be utilized.

The motor 66 is electrically connected to an electronic controller and power supply 68 that is shown schematically in FIGS. 6–9. A momentary contact motor operation switch 70 (FIG. 1) is located on the upper front side of the housing 22 and is electrically connected to the controller and power supply 68. When the switch 70 is moved to one position, the motor 66 is energized and rotates the drive screw 62 in one direction in order to raise the platen 56 and collapse the containers 30, 32. Movement of the switch 70 to the other position causes the motor 66 to turn the drive screw in an opposite direction and thus lower the platen 56 as might occur, for example, when the containers 30, 32 are substantially empty.

The system 20 is also provided with indicator lamps 72 that are located on the upper front side of the housing 22 next to the switch 70 as illustrated in FIG. 1. The indicator lamps 72 are connected to the controller and power supply 68. One lamp 72 indicates whether or not power is supplied to the controller and power supply 68. Another lamp 72 is activated when the platen 56 is in a certain vertical position in order to indicate that the quantity of components remaining in the containers 30, 32 is exhausted, or nearly exhausted. The third lamp 72 is energized as described below.

Each of the tubings 42, 54 include a rigid section 74 that is connected to the couplers 40, 50, as well as a flexible section 76 that extends along the inner side of the top of the housing 22. The tubings 42, 54 also each include a rigid fill tube 78 that is slidably received in a guide bushing 80 (see FIGS. 7–9) that is fixed to the housing 22.

The fill tubes 78 are connected together by a link 82 (see FIG. 8) that is also connected to a vertically slidable operating lever 84 located on the front wall of the housing 22. When the lever 84 is depressed, the fill tubes 78 simultaneously descend along respective vertical axes, guided for movement by the bushings 80. The flexible sections of tubing 76 enable the fill tubes 78 to descend or ascend as needed.

Figure 10:
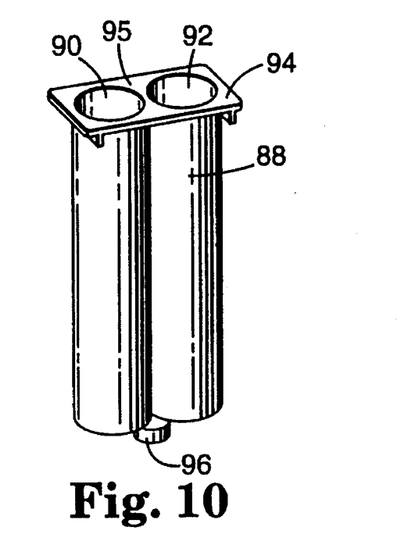
FIG. 10 is an enlarged perspective view of a dispensing cartridge of the refilling system.

The front of the housing 22 also includes a third, recessed receptacle 86 that matingly, releasably receives and supports a dual chamber dispensing cartridge 88. The cartridge 88 alone is shown in FIG. 10, and includes a pair of side-by-side, parallel barrels each having an elongated chamber. The first barrel has a first chamber 90 for receiving the first component, and the second barrel has a second chamber 92 for receiving the second component.

The dispensing cartridge 88 also includes a rear, generally rectangular flange 94 that is integrally connected to the barrels. One side of the flange 94 has a V-shaped notch or recess 95 that is received around a protruding tab 97 (FIGS. 7 and 9) fixed to the housing 22 in an upper, rear section of the third receptacle 86. The recess 95 and tab 97 substantially preclude placing the cartridge 88 in the third receptacle 86 in a reverse orientation where the fill tube 78 of the first tubing 42 is located over the second chamber 92 and vice versa. As a consequence, the first component can only be directed into the first chamber 90, and the second component can only be directed into the second chamber 92.

The cartridge 88 has a front, protruding outlet 96 having separated D-shaped channels that lead to respective chambers 90, 92. A cap 99 is detachably received over the outlet 96. A bottom, horizontal shelf of the third receptacle 86 is located from a top wall of the third receptacle 86 a distance that is closely complemental to the overall length of the cartridge 88 and the cap 99, such that the cartridge 88 may be securely retained in the third receptacle 86 without additional support or assistance by the user.

Figure 7:
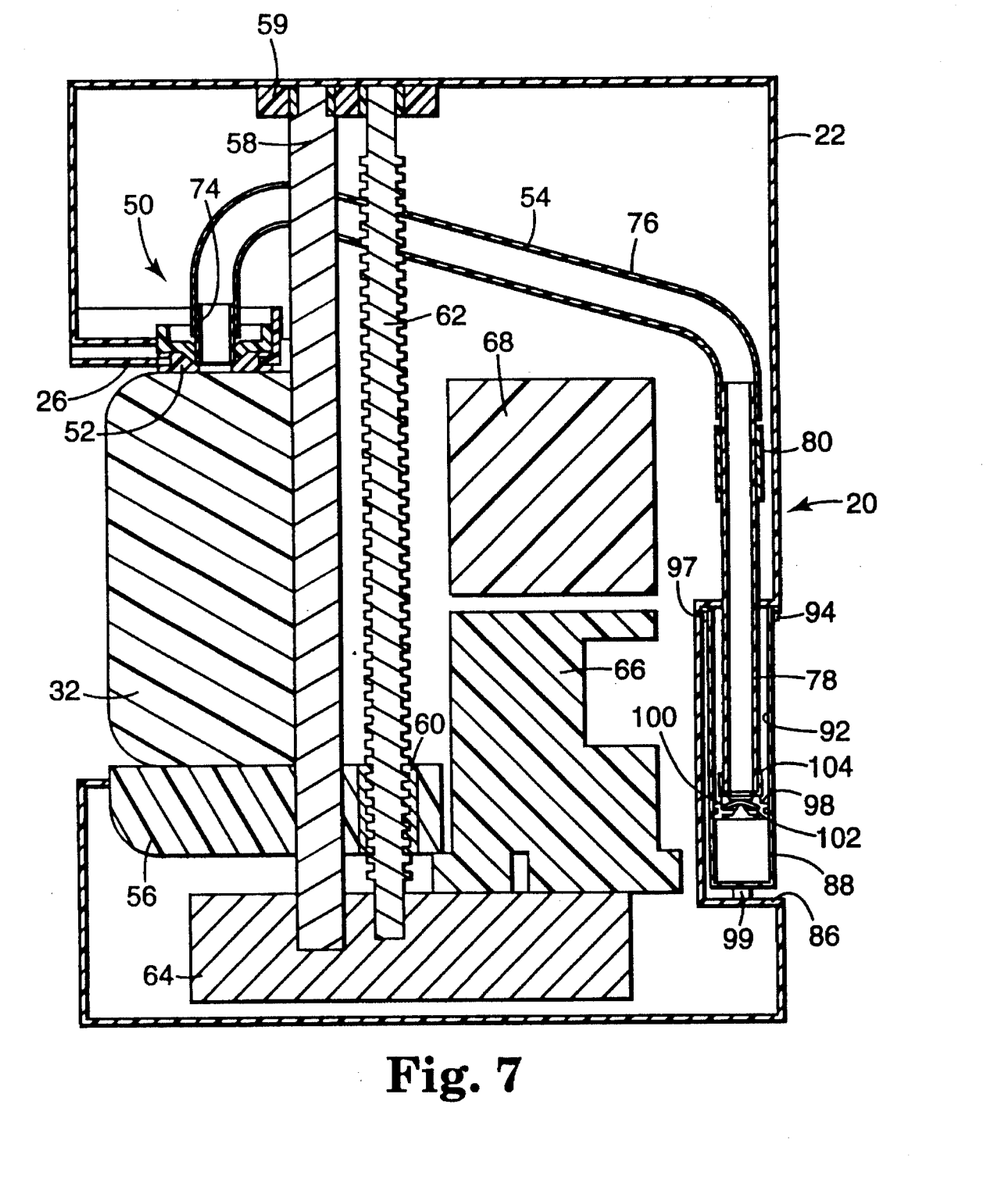
FIG. 7 is a side cross-sectional view of the system shown in FIG. 6, except that a fill tube of the system has been lowered into a chamber of a dispensing cartridge for releasable connection with a port of a cartridge piston.
Figure 9:
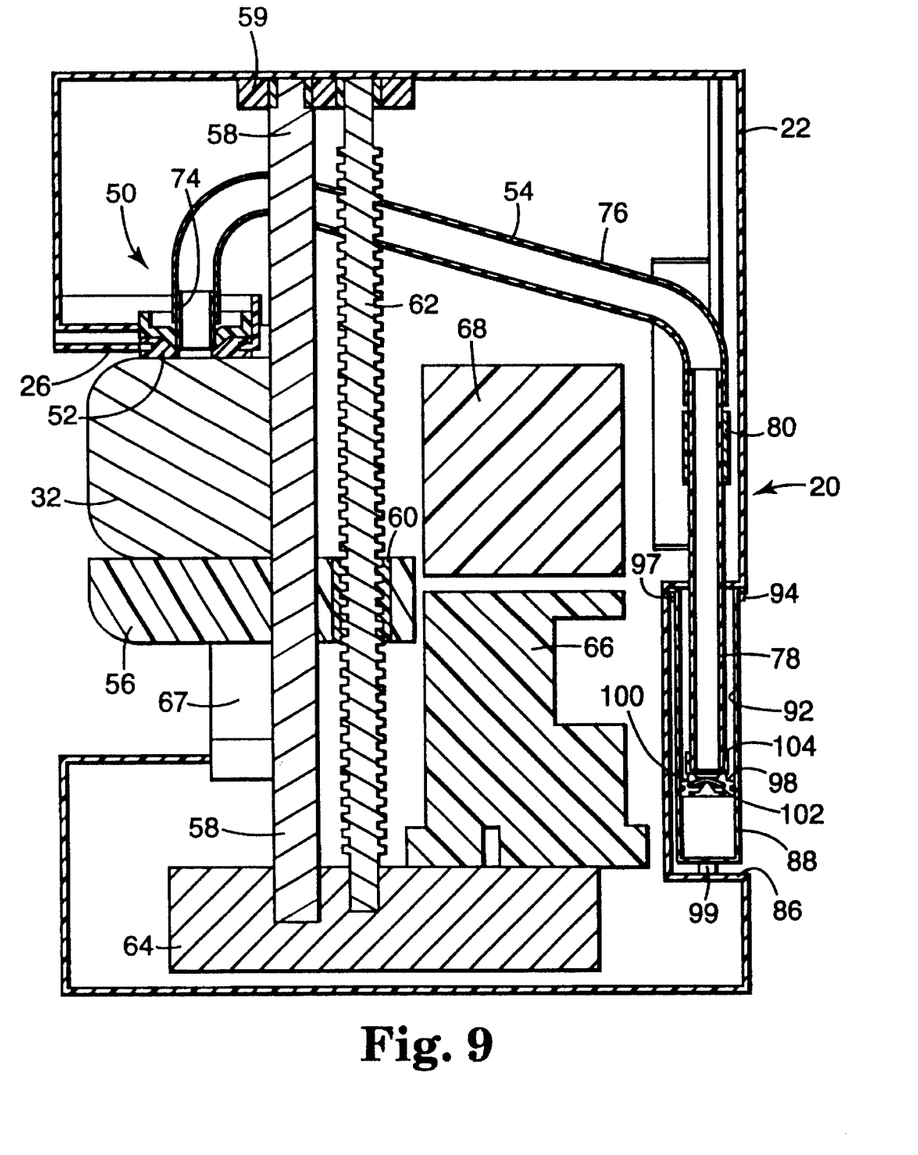
FIG. 9 is a view somewhat similar to FIG. 7 except that the bulk container and an underlying, supporting pumping platen are shown as they appear after a number of refilling operations.

Each of the chambers 90, 92 contains about 25 ml of a component. The chambers 90, 92 each receives a piston 98, one of which is shown in FIGS. 7 and 9. Each piston includes an inner port 100 and a check valve 102 located in the port 100. The check valve 102 includes a flexible valve member made of, for example, spring steel or resilient plastic. The valve 102 opens when refilling the chambers 90, 92 to enable the passage of a component through the port 100 in a downwardly direction viewing FIGS. 7 and 9. When refilling has ceased, the valve self-closes to preclude passage of a component in an opposite direction.

The lower end of each fill tube 78 includes a connector 104 for releasably connecting the tubing 42, 54 to the pistons 98 whenever refilling of the cartridge 88 is desired. The lower end of the connector 104 includes a cylindrical projection that is slidably received in a complementally-sized cylindrical bore in the upper portion of the port 100. The fill tubes 78 are connected to the pistons 98 by lowering the lever 84 until such time as the connector 104 couples with the pistons 98.

Preferably, each connector 104 includes a spring-biased poppet valve similar to the valves commonly used on automotive and bicycle tire tubes. The poppet valves are normally closed when the connectors 104 are not coupled to the pistons 98, so that the components are not inadvertently discharged from the fill tubes 78. However, once the connectors 104 are securely coupled to the pistons 98, an upstanding pin (not shown) of the pistons 98 contacts the valve stem of the poppet valves in order to open the latter and permit the components to flow through the tubings 42, 54, past the poppet valves, into the ports 100 and past the check valves 102 and into portions of the chamber 90, 92 below the pistons 98.

Other connectors as alternatives to connectors 104 may also be provided. For example, such connectors could include a rotational coupling such as a bayonet-type coupling, threaded coupling or the like that secures the fill tubes 78 to the pistons 98 when the fill tubes 78 are rotated relative to the pistons 98. In such instances, a lever arm or other means would be provided to rotate the fill tube 78 and/or the connectors relative to the pistons 98 to effect the coupling.

As the chambers 90, 92 are refilled, the pistons 98, the fill tubes 78 and the lever 84 rise in unison. A microswitch (not shown) is triggered when the lever 84 reaches a certain height, and energizes the third lamp 72 to indicate that the cartridge chambers 90, 92 are full.

Means is also provided for substantially preventing undue pressure in the tubings 42, 54 as might occur, for example, when the chambers 90, 92 of the cartridge have been filled and the motor 66 continues to run, or when the fill tubes 78 have not been properly connected to the piston ports 100 such that the poppet valves have not opened. Preferably, such means is provided by a slip clutch in the gear mechanism 64. The slip clutch uncouples the motor 66 from the drive screw 62 whenever torque required to turn the drive screw 62 exceeds a certain, predetermined value. As an alternative, each tubing 42, 54 may be provided with pressure sensors electrically coupled to the controller and power supply 68 and operable to de-energize the motor 66 whenever pressure in the tubings 42, 54 exceeds a certain value.

Electronic or optical interlocks or sensors may also be connected to the controller and power supply 68 to insure proper operation. For example, the microswitch used to activate the third lamp 72 may be connected to the controller 68 to prevent ascension of the platen 56 when the cartridge 88 is full. Alternatively, microswitches interconnected with the controller 68 may include a probe that detects the position of the fill tubes 78 in order to prevent ascension of the platen 56 when the pistons 98 are at the top of the respective chambers 90, 92, or when the fill tubes 78 are in the position shown in FIG. 6 and out of engagement with the pistons 98. Microswitches or optical sensors may also be provided to detect the presence of the cartridge 88 in the third receptacle 86; if the absence of a cartridge 88 is detected, a connecting rod of a solenoid-actuated latching assembly (not shown) mechanically intercepts the link 82, so that depression of the lever 84 and the fill tubes 78 is precluded.

Optical, electronic or mechanical sensors may also be provided to detect the presence of containers 30, 32 and confirm that the first container 30 is not in the second receptacle 26 and vice versa. The detectors may include a bar code sensor to read bar code information located on the containers 30, 32, or may include a color detector or other optical detector that senses the presence or absence of colors or other features on the containers 30, 32. At any time that containers 30, 32 are not properly received in respective receptacles 24, 26, the controller and power supply 68 prevents actuation of the motor 66 in one direction so that ascension of the platen 56 to a height sufficient to collapse the containers 30, 32 is prohibited.

Similarly, optical, electronic or mechanical sensors may be used to determine when the platen 56 has reached its upper or lower limit along its path of travel, so that further energization of the motor 66 in the same direction is prohibited. As an alternative, the gear mechanism 64 may include a slip clutch (such as the one mentioned hereinabove) to prevent further rotation of the drive screw 62 once the platen 56 has reached its upper or lower limit along its path of travel.

Alternative structure may also be provided as means for directing the components through the tubing 42, 54, through the fill tubes 78 and into the chambers to refill the cartridge 88. For example, containers 30, 32 may be surrounded by a rubber sleeve that is inflatable to compress the containers 30, 32 and eject components through the tubing 42, 54. A piston pump or squeeze tube pump may also be employed. As another option, the containers 30, 32 may be replaced by a dual chamber cartridge that is similar to the cartridge 88 but much larger in size; in such an instance, a hand powered or electric motor powered ratchet mechanism may be utilized to force material from the dual chamber bulk cartridge and into the dispensing cartridge 88.

Refilling of the cartridge 88 from a location rearwardly of the outlet 96 is presently preferred, so that small amounts of components remaining in the chambers 90, 92 are dispensed first during the next dispensing operation after refilling the cartridge 88. As a result, the components move through the chambers 90, 92 in first-in, first-out manner. As an alternative, however, the cartridge 88 may be refilled through the outlet 96 using slender filling tubes.

Other means are also possible for refilling the cartridge 88 rearwardly of the outlet 96. For example, the chambers 90, 92 are refilled after hand-removing the pistons. Alternatively, the chambers 90, 92 are refilled through facing, front, side inlet ports in detachable barrels of the cartridge that are exposed when the barrels are separated from one another. As another option, the barrel chambers are refilled through front, non-facing side inlet ports or through front end ports (spaced from the outlet 96) that are then plugged for a subsequent dispensing operation.

Optionally, the motor 66 may be replaced by a lever and ratchet mechanism for hand or foot operation. Other alternatives include DC motors or compressed air powered piston and cylinder assemblies that are linked to the platen 56.

Likewise, movement of the fill tubes 78 may also be carried out by an electric motor, compressed air or a solenoid. As an alternative to moving the fill tubes 78, the third receptacle 86 may instead be movable so that the cartridge 88 can be moved to a position wherein the fill tubes 78 extend into the chambers 90, 92.

As another option, the cartridge 88 is installed by hand onto the fill tubes which could be fixed or movable, and which could be upstanding or depending. In this regard, the word "receptacle" as used herein should be understood to mean any location that receives the cartridge 88 for refilling, and should not be limited to a recessed receptacle or a receptacle within a housing or the like.

A preferred hand-held automated cordless dispenser for receiving the cartridge 88 and dispensing the first and second components is described in a co-pending U.S. patent application entitled "Automated Hand-Held Dispenser for Dual Chamber Cartridge", U.S. Ser. No. 08/287,874, filed on even date herewith. As an alternative, the cartridge 88 may be used in conjunction with a hand-powered ratchet-type applicator such as is described in pending U.S. patent application Ser. No. 08/204,989 entitled "Dual Chamber Cartridge Dispensing System for Dental Material".

The refilling system 20 is particularly advantageous in instances where it is desired that the dispensing operation be carried out without interruption. For example, in a procedure involving dispensing of dental impression material, it may be desirable to first refill the cartridge 88 so that the cartridge 88 need not be replaced or refilled during the middle of the procedure. The refilling system 20 enables the practitioner to begin each procedure with a filled cartridge, and obviates the need to dispose of a cartridge that has been used but not completely emptied of components.

Other advantages of the invention are also apparent. For one thing, a savings in cost may be realized by purchasing the components in inexpensive bulk containers such as containers 30, 32. Also, the cartridges 88 can be reused a number of times and need not be discarded after a single use.

Figure 11:
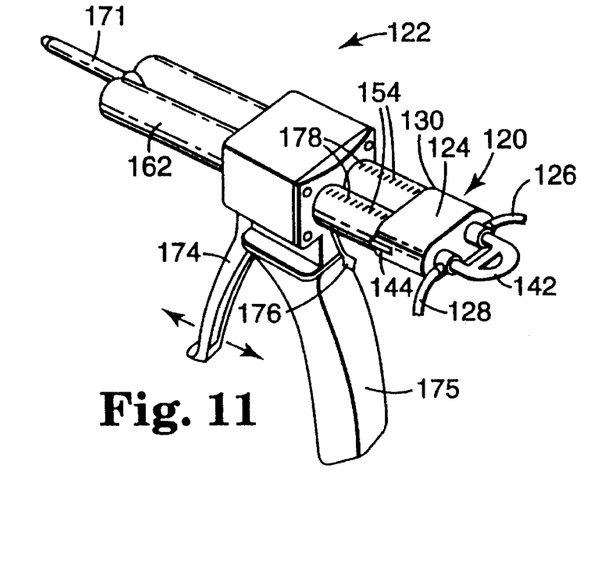
FIG. 11 is a perspective view of a dual chamber dispenser and dispenser refilling system assembly in accordance with another embodiment of the invention.
Figure 12:
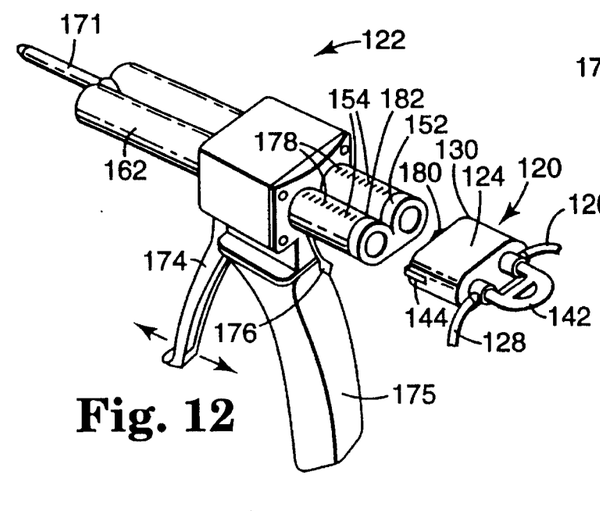
FIG. 12 is a view somewhat similar to FIG. 11 except that a refilling head of the refilling system has been disconnected from plungers of the dual chamber dispenser.

Another embodiment of the invention is illustrated in FIGS. 11 and 12, wherein a refilling system 120 is especially adapted for use with a dispenser 122. The refilling system 120 includes a refilling head 124 that is connected to a first flexible tube 126 and a second flexible tube 128. Tubes 126, 128 are coupled to a source of a first component and a source of a second component respectively.

One option as sources for the first and second component is a pumping system that is similar to the refilling system 20 shown in FIGS. 1–9, except that the third receptacle 86, the lever 84, the rigid fill tubes 78 and other elements associated with refilling the cartridge 88 are omitted. Instead, the first tubing 42 is directly coupled to the first tube 126 and the second tubing 54 is directly coupled to the second tube 128. As such, activation of the switch 70 causes the first and second component to be directed through the first tube 126 and second tube 128 respectively.

Figure 13:
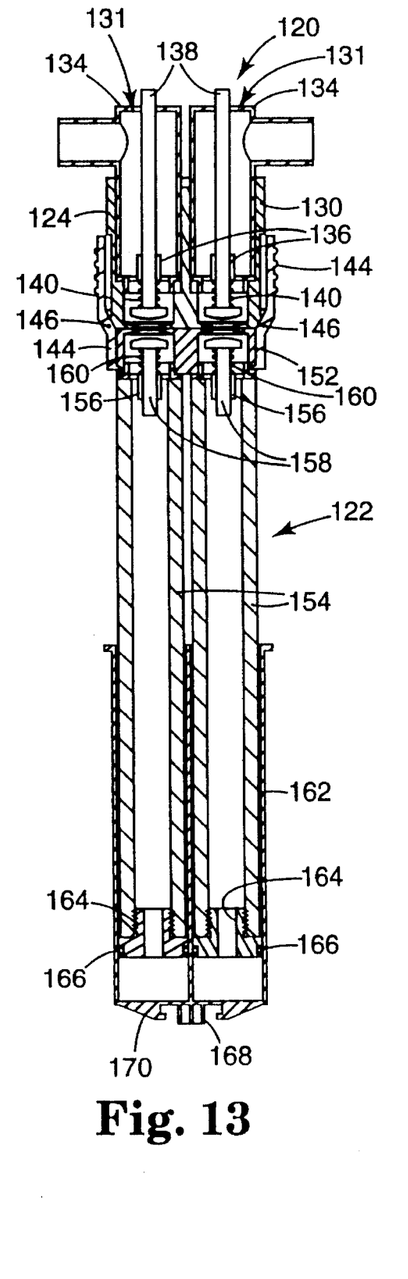
FIG. 13 is an enlarged, cross-sectional view of the refilling head of the refilling system and the plungers and a cartridge of the dual chamber dispenser illustrated in FIG. 11.
Figure 14:
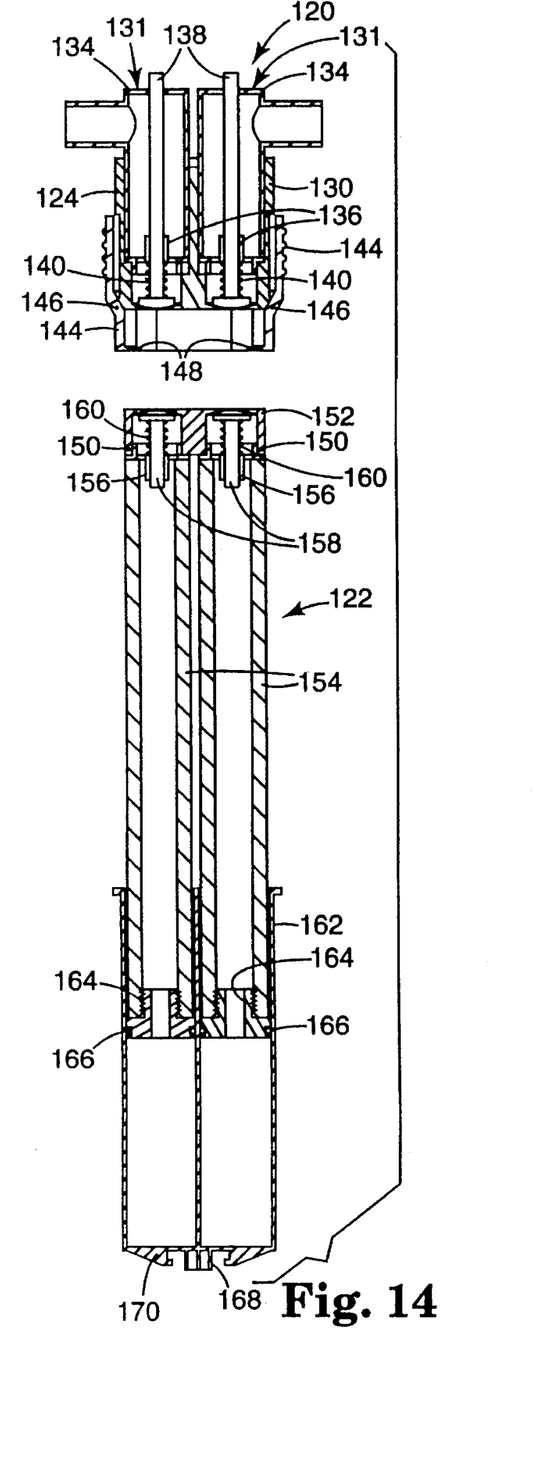
FIG. 14 is a view somewhat similar to FIG. 13 except that the refilling head has been disconnected from the plungers.

The refilling head 124 includes a hollow shell 130 (FIG. 14) with two values 13. Two valve bodies 134 are secured to interior cavities of the shell 130 and each has a side port that is coupled to one of the tubes 126, 128. As shown in FIGS. 13–14, a bushing 136 is located in each valve body 134 and slidably receives a valve stem 138. One end of each stem 138 is fixed to a valve head, and the other end of each stem 138 extends through the corresponding valve body 134.

Each valve head is biased by a coil spring 140 to a closed position in sealing contact with a valve seat of the shell 130. Each spring 140 is captured in place on the stem 138 between the corresponding bushing 136 and the valve head. Both of the stems 138 are fixed to a handle 142 (FIGS. 11–12 only) that is movable relative to the shell 130 to simultaneously open the valve heads when desired. Optionally, a solenoid could be provided to move the valve stems 138 and open the valve heads.

A releasable connection for coupling the dispenser 122 to the refilling system 120 includes a pair of levers 144 that are each connected to the shell 130 by a pivot 146. Each lever 144 has a ribbed end section and an opposite end section having an inwardly extending, pointed catch 148 (FIG. 14). A spring (not shown) biases each lever 144 in a spring (not shown) biases each lever 144 in a direction that urges the catch 148 in releasable locking engagement with a mating cavity 150 (see FIG. 14) formed in an end piece 152 of the dispenser 122. The shell 130 is detached from the end piece 152 when desired by depressing the ribbed end sections of the levers 144 in order to release each catch 148 from the corresponding cavity 150.

The dispenser 122 has two hollow, elongated, side-by-side parallel plungers 154 that are affixed at their rearward ends to the end piece 152. A guide bushing 156 is located in each plunger 154, and receives a valve stem 158 of a check valve assembly. A valve head is coupled to each valve stem 158 and is biased by a spring 160 toward a closed position in sealing contact with a respective valve seat of the end piece 152.

The dispenser 122 includes a cartridge 162 having parallel, elongated, side-by-side barrels that slidably receive the plungers 154. Each plunger 154 includes a fitment 164 having a central passage that communicates the interior of the plunger 154 with the chamber within each corresponding barrel of the cartridge 162. Each fitment 164 has a peripheral groove that receives an O-ring 166 in sealing contact with inner cylindrical sidewalls of the barrels.

A front end of the cartridge 162 has an outlet port 168 with separated, D-shaped outlet passageways that each lead to a respective barrel chamber. The front end of the cartridge 162 also includes a bayonet connection 170 for detachably receiving an exit conduit having a static (or optionally dynamic) mixer 171 (FIGS. 11–12). If desired, a swivelable discharge tip may be coupled to the forward end of the exit conduit to facilitate placing the discharged, mixed material onto a desired location.

Figure 15:
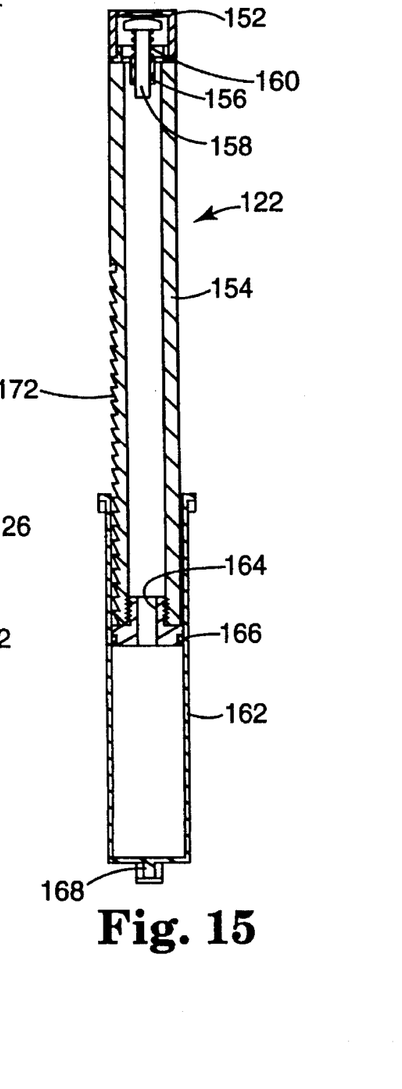
FIG. 15 is an enlarged side cross-sectional view of the plungers and cartridge alone that are shown in FIGS. 13 and 14.

As depicted in FIG. 15, an underside of each plunger 154 includes a toothed rack 172 for driving engagement with a ratchet-type drive mechanism of the dispenser 122. The drive mechanism is not shown in the drawings, but can be similar to existing ratchet-type drive mechanisms that are well known to those skilled in the art for use with double-barrel dispensing cartridges such as the cartridge illustrated in U.S. Pat. No. 4,538,920. An alternative drive mechanism (and barrel orientation) is described in the aforementioned pending U.S. patent application Ser. No. 08/204,989. As another option, a cordless electric motor drive mechanism, or a pressurized carbon dioxide canister piston-and-cylinder drive mechanism may be provided.

A pivoting front lever arm 174 (FIGS. 11–12) of the dispenser 122 is connected to the drive mechanism. When the lever arm 174 is squeezed toward a stationary, depending rear grip 175, the drive mechanism advances the plungers 154 in a direction toward outlet port 168 and directs components in the barrel chambers through the outlet passageways of the outlet port 168. During dispensing, pressure within the plungers 154 and the barrel chambers retains the valve head of each check valve assembly in closed, sealing engagement with the valve seats of the end piece 152. When the lever arm 174 is released, a spring urges the lever arm 174 to a forward position.

When refilling of the dispenser 122 is desired, the refilling head 124 is coupled to the end piece 152 by depressing the levers 144 and sliding the shell 130 over the end piece 152 until the catches 148 engage the cavities 150. The levers 144 are then released, and the handle 142 is pulled rearwardly in a direction away from the dispenser 122 in order to open the valve heads in the valve bodies 134. Next, the refilling system is operated to urge the first and second components through the first and second tubes 126, 128 respectively in a direction toward the chambers of the plungers 154.

The user then presses a tab 176 (FIGS. 11–12) located on a rear side of a housing for the dispenser 122. Depression of the tab 176 releases pawls of the ratchet-type drive mechanism from the racks 172 to enable the plungers 154 to move freely in a rearwardly direction relative to the cartridge 162 as the cartridge 162 is refilled.

As the first and second components are directed into the chambers of the plungers 154, the check valve assemblies in each plunger 154 open. As the components enter the chambers of the plungers 154, the plungers 154 move rearwardly from their positions shown in FIG. 13 and to their positions shown in FIG. 14. Although not shown, an arm connected to the plungers 154 is engageable with the housing of the dispenser 122 as the plungers 154 move rearwardly, in order to prevent the plungers 154 from disengaging and separating from the cartridge 162.

A cap (not shown) having a bayonet-style coupling is connected to the bayonet connection 170 of the cartridge 162 to prevent the components from discharging through the outlet port 168 as the cartridge 162 is refilled. As an alternative, a previously used exit conduit (such as conduit 171) that is filled with hardened, cured material can be used in place of the cap.

Once refilling of the dispenser 122 has been accomplished, pressure on the tab 176 and on the handle 142 is released. Next, the levers 144 are depressed and the refilling head 124 is uncoupled from the dispenser 122.

The cartridge 162 may be non-removably connected to the housing of the dispenser 122, or alternatively may be removably connected by a rear flange of the cartridge 162 that engages channels of the dispenser housing. Preferably, and as shown in FIGS. 11–12, the top of the plungers 154 bear a series of indicia 178. As the plungers 154 advance forward during dispensing, the indicia 178 that are exposed and rearward of the dispenser housing serve to indicate to the user the quantity of components remaining in the dispenser 122.

The dispenser 122 is especially advantageous in that fresh components are introduced into the rear of the plungers 154 when the dispenser 122 is refilled. As a consequence, the components move through the dispenser 122 in first-in, first-out fashion. As an alternative to the tethered refilling head 124 shown in the drawings, it is also possible and within the scope of the invention to affix the refilling head 124 directly to a housing of the refilling system, such as housing 22 illustrated in FIGS. 1–2 and 6–9.

The refilling head 124 also includes a forwardly projecting pin 180 (FIG. 12) that is received in a recess 182 of the dispenser end piece 152. Since only one pin and recess are provided, the refilling head 124 can only be connected to the dispenser 122 in the orientation shown in FIG. 11, and not in a reverse orientation. As a consequence, the first component is precluded from entering the chamber of a plunger that has previously received a quantity of the second component.

Other alternatives to the specific embodiments described above may also be envisioned. Accordingly, the scope of the invention should be not limited to the specific embodiments described above, but instead should be determined by a fair reading of the claims that follow and their equivalents.

What is claimed is:

1. A dual chamber dispensing cartridge refilling system comprising:

a housing having a first receptacle, a second receptacle and a third receptacle;

a first container releasably received in said first receptacle and containing a quantity of a first component;

a second container releasably received in said second receptacle and containing a quantity of a second component;

a dual chamber dispensing cartridge releasably received in said third receptacle, said cartridge including a first elongated chamber for receiving the first component and a second elongated chamber for receiving the second component;

first tubing in communication with said first container when said first container is received in said first receptacle, said first tubing being in communication with said first chamber of said cartridge when said cartridge is received in said third receptacle;

second tubing in communication with said second container when said second container is received in said second receptacle, said second tubing being in communication with said second chamber of said cartridge when said cartridge is received in said third receptacle;

means for directing the first component from said first container, through said first tubing and into said first chamber, and for directing the second component from said second container, through said second tubing and into said second chamber; and structure for substantially precluding said second container from being received in said first receptacle in order to avoid directing the second component into said first chamber of said cartridge.

2. The system of claim 1, wherein said structure includes a tab connected to said housing for contact with said cartridge as said cartridge is received in said third receptacle.

3. The system of claim 1, wherein said structure comprises a coupler for coupling said first tubing to said first container.

4. The system of claim 3, wherein said first container includes a neck, and wherein said coupler includes a movable element and a spring for urging said element toward a position in contact with said neck when said first container is received in said first receptacle.

5. The system of claim 3, wherein said first connector includes a neck with a keyway, and wherein said structure includes a hole in said coupler for receiving said keyway.

6. The system of claim 3, wherein said first container includes a neck having at least one thread, and wherein said structure includes a threaded portion for contact with said at least one thread.

7. The system of claim 1, and including a movable platen, and wherein said first container and said second container are in contact with said platen and are collapsible upon movement of said platen.

8. The system of claim 1, wherein said first tubing includes a relatively rigid first fill tube and wherein said second tubing includes a relatively rigid second fill tube, and wherein said first fill tube and said second fill tube are movable relative to said housing for selective extension into said chambers of said cartridge.

9. The system of claim 8, wherein said cartridge includes a piston received in said first chamber and a piston received in said second chamber, and wherein said pistons include a port for contact with said first fill tube and said second fill tube as said first fill tube and said second fill tube are moved relative to said housing.

10. A dual chamber dispensing cartridge refilling system comprising:

a housing having a first receptacle, a second receptacle and a third receptacle;

a first container releasably received in said first receptacle and containing a quantity of a first component;

a second container releasably received in said second receptacle and containing a quantity of a second component;

a dual chamber dispensing cartridge releasably received in said third receptacle, said cartridge including a first elongated chamber for receiving a first component and a second elongated chamber for receiving a second component;

a first elongated fill tube, said first fill tube being in communication with said first container when said first container is received in said first receptacle;

a second elongated fill tube, said second fill tube being in communication with said second container when said second container is received in said second receptacle;

means for selectively moving said first fill tube and said second fill tube relative to said cartridge and to respective orientations wherein said first fill tube extends into said first chamber and said second fill tube extends into said second chamber;

means for directing the first component from said first container, through said first fill tube and into said first chamber, and for directing the second component from said second container, through said second fill tube and into said second chamber; and structure for substantially precluding said first fill tube from extending into said second chamber.

11. The system of claim 10, wherein said structure comprises a tab connected to one of said housing and said cartridge for contact with the other of said housing and said cartridge as said cartridge is received in said third receptacle.

12. The system of claim 11, wherein said tab is connected to said housing and is received in a recess of said cartridge.

13. The system of claim 10, wherein said means for directing the first component and the second component includes a movable platen in contact with said first container and said second container.

14. The system of claim 10, wherein said means for selectively moving said first fill tube and said second fill tube comprises a link interconnecting said first fill tube and said second fill tube, and a lever connected to said link.

15. The system of claim 10, wherein said first container and said second container are spaced apart from each other.

16. The system of claim 10, wherein said first container is integrally connected to said second container.

17. The system of claim 10, and including structure for substantially precluding said second container from being received in said first receptacle in order to avoid directing of the second component into said first chamber of said cartridge.

18. A dispensing cartridge refilling system comprising:

a housing having a receptacle;

a dispensing cartridge releasably received in said receptacle, said cartridge including an elongated chamber for receiving material to be dispensed, said cartridge including a piston received in said chamber;

a source of material to be dispensed;

a fill tube in communication with said source of material, at least one of said fill tube and said cartridge being selectively movable relative to the other and to an orientation wherein said fill tube extends into said chamber, said piston including a port in contact with said fill tube when said fill tube extends into said chamber for enabling material to be directed through said fill tube, through said port and into said chamber; and a connector coupled to said fill tube, wherein said connector is releasably connectable to said port of said piston, and wherein said connector includes a valve.

19. The system of claim 18, wherein said piston includes a check valve.

20. The system of claim 18, wherein said source of material includes a container containing the material, wherein said container is collapsible, and including a movable platen in contact with said container for collapsing said container.

21. A dispensing cartridge refilling system comprising:

a housing having a receptacle;

a dispensing cartridge releasably received in said receptacle, said cartridge including an elongated chamber for receiving material to be dispensed, said cartridge including a piston received in said chamber;

a source of material to be dispensed;

a fill tube in communication with said source of material, at least one of said fill tube and said cartridge being selectively movable relative to the other and to an orientation wherein said fill tube extends into said chamber, said piston including a port in contact with said fill tube when said fill tube extends into said chamber for enabling material to be directed through said fill tube, through said port and into said chamber; and a lever connected to said fill tube for selectively moving said fill tube relative to said housing and into said chamber.

22. The system of claim 21, including a guide bushing surrounding said fill tube for guiding the movement of said fill tube.

23. The system of claim 21, wherein said fill tube is relatively rigid, and including a length of flexible tubing connected to and communicating with said relatively rigid fill tube.

24. A cartridge refilling system comprising:

a housing having a receptacle;

a container releasably received in said receptacle and containing a quantity of material to be dispensed, said container including a neck;

tubing connected to said housing, said tubing including a first end located next to said receptacle and a second end for communication with a cartridge to be refilled; and a coupler for releasably coupling said neck of said container to said first end of said tubing, said coupler including a movable element a and spring for urging said element toward a position in contact with said neck when said container is received in said receptacle, said coupler including a generally U-shaped support for receiving said neck in a direction laterally of the movement of said element when said element is urged by said spring toward said position of contact with said neck.

25. The container of claim 24, wherein said container includes a collapsible wall portion.

26. The container of claim 25, wherein said container is elongated and collapsible in a direction along its longitudinal axis.

27. The system of claim 25, including a platen in contact with said container, wherein said platen is movable for collapsing said container.

28. A dual chamber dispenser and dispenser refilling system assembly comprising:

a dispenser having a cartridge with a first chamber, a second chamber, a first plunger received in said first chamber, and a second plunger received in said second chamber;

a dispenser refilling system comprising a source of a first component and a source of a second component;

a connector for releasably connecting said dispenser to said refilling system;

means for directing said first component from said source of first component and into said first chamber of said dispenser, and for directing said second component from said source of second component and into said second chamber of said dispenser; and structure for substantially precluding said second component from being received in said first chamber.

29. The assembly of claim 28, wherein said first plunger and said second plunger are hollow, and wherein said connector releasably connects said refilling system to said first plunger and said second plunger.

30. The assembly of claim 29, wherein said refilling system includes a refilling head and a length of flexible tube that connects said refilling head to said source of first component and said source of second component.

31. The assembly of claim 30, wherein said refilling head includes valves for controlling the flow of said first component and said second component.

32. The assembly of claim 28, wherein said dispenser includes a housing, and wherein said cartridge is releasably connected to said housing.

33. The assembly of claim 28, wherein said dispenser includes a housing, and wherein said cartridge is non-releasably connected to said housing.

* * * * *